United States Patent
Wang et al.

(10) Patent No.: US 12,044,631 B2
(45) Date of Patent: Jul. 23, 2024

(54) WAFER SURFACE DEFECT INSPECTION METHOD AND APPARATUS THEREOF

(71) Applicant: GlobalWafers Co., Ltd., Hsinchu (TW)

(72) Inventors: Shang-Chi Wang, Hsinchu (TW); Miao-Pei Chen, Hsinchu (TW); Han-Zong Wu, Hsinchu (TW); Chia-Chi Tsai, Hsinchu (TW); I-Ching Li, Hsinchu (TW)

(73) Assignee: GlobalWafers Co., Ltd., Hsinchu (TW)

( * ) Notice: Subject to any disclaimer, the term of this patent is extended or adjusted under 35 U.S.C. 154(b) by 24 days.

(21) Appl. No.: 17/574,565

(22) Filed: Jan. 13, 2022

(65) Prior Publication Data
US 2022/0307991 A1  Sep. 29, 2022

(30) Foreign Application Priority Data
Mar. 26, 2021 (TW) .................. 110111209

(51) Int. Cl.
*G01N 21/95* (2006.01)
*G01B 11/30* (2006.01)
*G01N 21/88* (2006.01)

(52) U.S. Cl.
CPC ......... *G01N 21/9501* (2013.01); *G01B 11/30* (2013.01); *G01B 11/303* (2013.01);
(Continued)

(58) Field of Classification Search
CPC ............... G01N 21/88; G01N 21/8803; G01N 21/8806; G01N 21/892; G01N 21/8921; G01N 21/8922; G01N 21/94; G01N 21/9501; G01N 21/9503; G01N 2021/8809; G01N 2021/8835; G01N 2021/8854; G01N 2021/8858; G01N 2021/8861; G01N 2021/8864; G01N 2021/8867;
(Continued)

(56) References Cited

U.S. PATENT DOCUMENTS

| 4,541,011 A | * | 9/1985 | Mayer | .................... G01N 21/89 |
| | | | | 348/133 |
| 4,597,228 A | * | 7/1986 | Koyama | ............. H01L 21/6838 |
| | | | | 451/388 |

(Continued)

FOREIGN PATENT DOCUMENTS

| JP | 2002228596 A | * | 8/2002 |
| JP | 2017219409 | | 12/2017 |

(Continued)

*Primary Examiner* — Gordon J Stock, Jr.
(74) *Attorney, Agent, or Firm* — JCIPRNET

(57) ABSTRACT

A wafer surface defect inspection method and a wafer surface defect inspection apparatus are provided. The method includes the following steps. Scanning information of a wafer is received, and the scanning information includes multiple scanning parameters. At least one reference point of the scanning information is determined, and path information is generated according to the at least one reference point and a reference value. Multiple first scanning parameters corresponding to the path information in the scanning parameters are obtained according to the path information to generate a curve chart. According to the curve chart, it is determined whether the wafer has a defect, and a defect type of the defect is determined.

20 Claims, 9 Drawing Sheets

(52) U.S. Cl.
CPC ....... *G01B 11/306* (2013.01); *G01N 21/8851* (2013.01); *G01N 2021/8861* (2013.01); *G01N 2021/8887* (2013.01)

(58) Field of Classification Search
CPC ..... G01N 2021/887; G01N 2021/8877; G01N 2021/888; G01N 2021/8887; G01N 2021/889; G01N 2021/8893; G01N 21/8851; G01N 2021/5581; G01N 2021/6664; G01N 2021/8875; G01N 2021/8924; G01N 2021/8925; G01N 2021/8928; G01B 11/30; G01B 11/303; G01B 11/306; G03F 7/70608; G03F 7/70616; G03F 7/7065
See application file for complete search history.

(56) References Cited

U.S. PATENT DOCUMENTS

| | | | | |
|---|---|---|---|---|
| 5,035,087 | A * | 7/1991 | Nishiguchi | B24B 49/16 451/287 |
| 5,319,570 | A * | 6/1994 | Davidson | G01B 11/306 702/170 |
| 5,955,654 | A * | 9/1999 | Stover | G01B 21/30 73/1.89 |
| 6,724,487 | B2 * | 4/2004 | Marcus | G01B 11/303 356/497 |
| 7,002,674 | B2 * | 2/2006 | Yokoyama | G01N 21/9501 356/237.2 |
| 7,433,031 | B2 * | 10/2008 | Xu | G01N 21/8806 356/338 |
| 7,528,944 | B2 * | 5/2009 | Chen | G03F 7/7065 356/237.1 |
| 7,605,915 | B2 | 10/2009 | Wolters et al. | |
| 7,659,974 | B2 * | 2/2010 | Bills | G01N 21/55 356/600 |
| 8,433,102 | B2 * | 4/2013 | Hayashi | G01N 21/9501 382/108 |
| 9,377,416 | B2 * | 6/2016 | Maleev | G01N 21/55 |
| 9,546,862 | B2 * | 1/2017 | Chen | G01B 11/24 |
| 9,922,414 | B2 * | 3/2018 | Takagi | G06T 7/001 |
| 10,180,316 | B2 * | 1/2019 | Brodmann | B23Q 17/003 |
| 10,416,086 | B2 * | 9/2019 | Kido | G01B 11/2513 |
| 10,782,242 | B2 * | 9/2020 | Muhr | G06T 7/001 |
| 10,943,048 | B2 * | 3/2021 | Nojima | H01L 22/12 |
| 10,964,014 | B2 * | 3/2021 | Chen | G03F 7/7065 |
| 11,852,465 | B2 * | 12/2023 | Wang | G01N 21/93 |
| 2010/0110419 | A1 | 5/2010 | Bills et al. | |
| 2011/0194753 | A1 * | 8/2011 | Kamiyama | G01N 21/8851 382/149 |
| 2011/0231129 | A1 * | 9/2011 | Yanai | H01L 22/20 702/81 |
| 2017/0178980 | A1 * | 6/2017 | Owen | G05B 19/41875 |
| 2017/0219807 | A1 | 8/2017 | Zhang | |
| 2019/0277776 | A1 * | 9/2019 | Gawhane | G01R 31/31728 |
| 2022/0270234 | A1 * | 8/2022 | Gu | G06T 7/0004 |
| 2022/0284562 | A1 * | 9/2022 | Benvegnu | H01L 21/30625 |
| 2022/0316872 | A1 * | 10/2022 | Wang | G01N 21/93 |

FOREIGN PATENT DOCUMENTS

| | | | |
|---|---|---|---|
| TW | I685652 | 2/2020 | |
| TW | I686602 | 3/2020 | |
| WO | WO-9602825 A1 * | 2/1996 | ....... G01N 21/95607 |
| WO | WO-2004072629 A1 * | 8/2004 | ......... G01B 11/0675 |
| WO | WO-2005050132 A1 * | 6/2005 | ........... G01N 21/956 |
| WO | WO-2006066135 A2 * | 6/2006 | ............. G01N 21/21 |
| WO | WO-2010050365 A1 * | 5/2010 | ............. B82Y 35/00 |
| WO | WO-2015156084 A1 * | 10/2015 | ............. G01B 11/06 |

* cited by examiner

WAFER SURFACE DEFECT INSPECTION METHOD AND APPARATUS THEREOF

CROSS-REFERENCE TO RELATED APPLICATION

This application claims the priority benefit of Taiwan application serial no. 110111209, filed on Mar. 26, 2021. The entirety of the above-mentioned patent application is hereby incorporated by reference herein and made a part of this specification.

BACKGROUND

Technical Field

The disclosure relates to a defect inspection technology of a semiconductor wafer, and more particularly to a wafer surface defect inspection method and a wafer surface defect inspection apparatus.

Description of Related Art

Before shipment from a factory, an electronic device to be tested is generally undergone visual inspection by a senior visual inspector in charge for determination by criteria such as whether an electronic device produced is defective or whether an electronic device is flat. For example, in determining flatness of a silicon carbide (SiC) wafer, a haze image of the silicon carbide wafer is usually obtained through automated optical inspection (AOI) equipment, and then the haze image is manually interpreted by human eyes.

However, there is no consistent standard in determination of visual inspection for the visual inspector to follow. Therefore, erroneous determination is often caused due to subjective determination by the visual inspector. Thus, how to avoid overly subjective inspection results due to excessive reliance on inspection by human eyes is indeed an issue of concern to people skilled in the art.

SUMMARY

The disclosure provides a wafer surface defect inspection method and a wafer surface defect inspection apparatus, which may automatically identify scanning information of a wafer and improve completeness and accuracy of defect inspection.

An embodiment of the disclosure provides a wafer surface defect inspection method, adapted for an electronic apparatus including a processor. The method includes the following steps. Scanning information of a wafer is received, and the scanning information includes multiple scanning parameters. At least one reference point of the scanning information is determined, and path information is generated according to the at least one reference point and a reference value. Multiple first scanning parameters corresponding to the path information in the scanning parameters are obtained according to the path information to generate a curve chart. According to the curve chart, it is determined whether the wafer has a defect, and a defect type of the defect is determined.

In an exemplary embodiment of the disclosure, the reference value includes at least one radius. In the step of determining the at least one reference point of the scanning information and generating the path information according to the at least one reference point and the reference value, a center of the wafer corresponding to the scanning information is calculated as the at least one reference point, and at least one circular path is determined according to the at least one radius based on the at least one reference point.

In an exemplary embodiment of the disclosure, in the step of obtaining the scanning parameters of the scanning information according to the path information to generate the curve chart, the first scanning parameters are obtained from pixels corresponding to the at least one circular path in the scanning information along a direction of the at least one circular path, and the curve chart is generated according to the first scanning parameters and a sequence of obtaining the first scanning parameters.

In an exemplary embodiment of the disclosure, the reference value includes a slice angle. In the step of determining the at least one reference point of the scanning information and generating the path information according to the at least one reference point and the reference value, a flat position of the scanning information and a center of the wafer corresponding to the scanning information are calculated. A median point of the flat position is calculated as a first reference point, and the center is used as a second reference point. A reference path is determined according to the first reference point and the second reference point, and a penetrating path is determined according to the reference path and the slice angle.

In an exemplary embodiment of the disclosure, in the step of determining the penetrating path according to the reference path and the slice angle, a rotation angle is calculated according to the slice angle, and the reference path is rotated according to the rotation angle to generate the penetrating path.

In an exemplary embodiment of the disclosure, in the step of obtaining the first scanning parameters corresponding to the path information in the scanning parameters according to the path information to generate the curve chart, the first scanning parameters are obtained from pixels corresponding to the penetrating path in the scanning information along a direction of the penetrating path, and the curve chart is generated according to the first scanning parameters and a sequence of obtaining the first scanning parameters.

In an exemplary embodiment of the disclosure, in the step of determining whether the wafer has a defect and determining the defect type of the defect according to the curve chart, a distance between each pair of adjacent wave peaks or each pair of adjacent wave troughs in the curve chart is calculated. If difference values between the distances are all less than a first threshold, and at least one of the first scanning parameters is greater than a second threshold, it is determined that the wafer has the defect. If at least one of the difference values between the distances is not less than the first threshold, and at least one of the first scanning parameters is greater than the second threshold, it is determined that the wafer has the defect. If the first scanning parameters are all not greater than the second threshold, it is determined that the wafer does not have the defect.

In an exemplary embodiment of the disclosure, the defect type includes at least one of a sun-like pattern, a zebra-like pattern, and a cloud-like pattern.

In an exemplary embodiment of the disclosure, the scanning parameter is generated by a scanning apparatus scanning the wafer, and the scanning parameter includes at least one of a haze value, a surface roughness value, and an image parameter.

In an exemplary embodiment of the disclosure, the image parameter includes at least one of a grayscale value, a luminance value, a contrast value, an RGB value, a saturation value, a color temperature value, and a Gamma value.

The disclosure provides a wafer surface defect inspection apparatus, including a connecting apparatus, a storage apparatus, and a processor. The connecting apparatus is used to connect a scanning apparatus to receive scanning information generated by the scanning apparatus scanning a wafer. The storage apparatus stores one or more instructions. The processor is coupled to the connecting apparatus and the storage apparatus, and is configured to execute the instruction for the following operations. The scanning information is received, and the scanning information includes multiple scanning parameters. At least one reference point of the scanning information is determined, and path information is generated according to the at least one reference point and a reference value. Multiple first scanning parameters corresponding to the path information in the scanning parameters are obtained according to the path information to generate a curve chart. According to the curve chart, it is determined whether the wafer has a defect, and a defect type of the defect is determined.

In an exemplary embodiment of the disclosure, the reference value includes at least one radius. In the operation of determining the at least one reference point of the scanning information and generating the path information according to the at least one reference point and the reference value, a center of the wafer corresponding to the scanning information is calculated as the at least one reference point, and at least one circular path is determined according to the at least one radius based on the at least one reference point.

In an exemplary embodiment of the disclosure, in the operation of obtaining the scanning parameters of the scanning information according to the path information to generate the curve chart, the first scanning parameters are obtained from pixels corresponding to the at least one circular path in the scanning information along a direction of the at least one circular path, and the curve chart is generated according to the first scanning parameters and a sequence of obtaining the first scanning parameters.

In an exemplary embodiment of the disclosure, the reference value includes a slice angle. In the operation of determining the at least one reference point of the scanning information and generating the path information according to the at least one reference point and the reference value, a flat position of the scanning information and a center of the wafer corresponding to the scanning information are calculated. A median point of the flat position is calculated as a first reference point, and the center is used as a second reference point. A reference path is determined according to the first reference point and the second reference point, and a penetrating path is determined according to the reference path and the slice angle.

In an exemplary embodiment of the disclosure, in the operation of determining the penetrating path according to the reference path and the slice angle, a rotation angle is calculated according to the slice angle, and the reference path is rotated according to the rotation angle to generate the penetrating path.

In an exemplary embodiment of the disclosure, in the operation of obtaining the first scanning parameters corresponding to the path information in the scanning parameters according to the path information to generate the curve chart, the first scanning parameters are obtained from pixels corresponding to the penetrating path in the scanning information along a direction of the penetrating path, and the curve chart is generated according to the first scanning parameters and a sequence of obtaining the first scanning parameters.

In an exemplary embodiment of the disclosure, in the operation of determining whether the wafer has a defect and determining the defect type of the defect according to the curve chart, a distance between each pair of adjacent wave peaks or each pair of adjacent wave troughs in the curve chart is calculated. If difference values between the distances are all less than a first threshold, and at least one of the first scanning parameters is greater than a second threshold, it is determined that the wafer has the defect. If at least one of the difference values between the distances is not less than the first threshold, and at least one of the first scanning parameters is greater than the second threshold, it is determined that the wafer has the defect. If at least one of the difference values between the distances is not less than the first threshold, and the first scanning parameters are all not greater than the second threshold, it is determined that the wafer does not have the defect.

In an exemplary embodiment of the disclosure, the defect type includes at least one of a sun-like pattern, a zebra-like pattern, and a cloud-like pattern.

In an exemplary embodiment of the disclosure, the scanning parameter is generated by the scanning apparatus scanning the wafer, and the scanning parameter includes at least one of a haze value, a surface roughness value, and an image parameter.

In an exemplary embodiment of the disclosure, the image parameter includes at least one of a grayscale value, a luminance value, a contrast value, an RGB value, a saturation value, a color temperature value, and a Gamma value.

Based on the above, the wafer surface defect inspection method and the wafer surface defect inspection apparatus provided in the disclosure may perform parameter extraction on scanning information of a wafer according to path information and analyze the extracted parameters to determine whether the wafer has a defect, thereby improving identification accuracy.

In order to make the aforementioned features and advantages of the disclosure comprehensible, embodiments accompanied with drawings are described in detail below.

DESCRIPTION OF THE EMBODIMENTS

Figure 1:
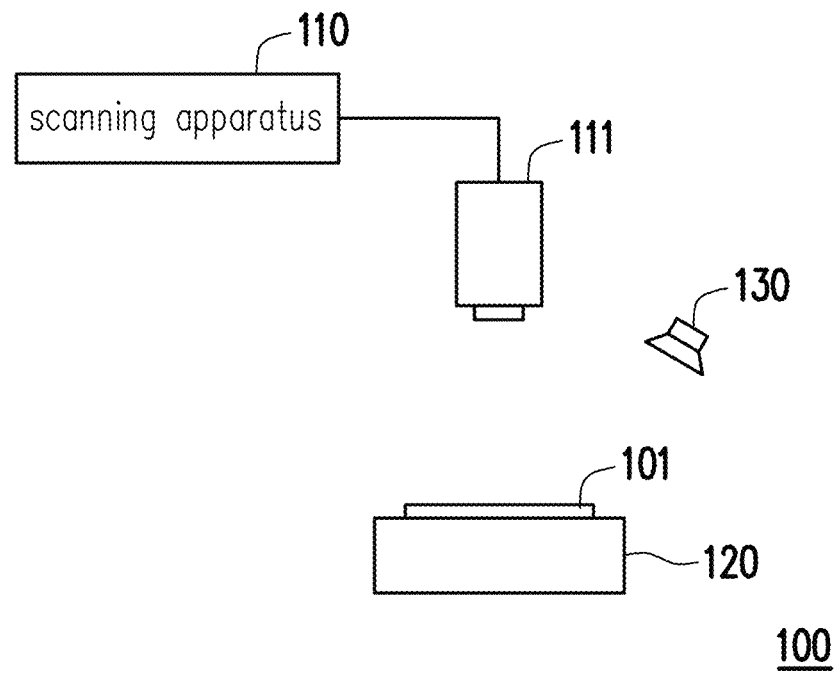
FIG. 1 is a schematic diagram of a wafer scanning system according to an embodiment of the disclosure.

FIG. 1 is a schematic diagram of a wafer scanning system according to an embodiment of the disclosure. With reference to FIG. 1, a wafer scanning system 100 may be applied to automated optical inspection equipment for scanning an object, such as a semiconductor chip, a wafer, a circuit board, a panel, or the like. In other words, the wafer scanning system 100 may be used to scan the surface of the object for scanning information of the surface of the object.

The wafer scanning system 100 may include a scanning apparatus 110, a transfer apparatus 120, and a light source apparatus 130. The scanning apparatus 110 has an optical lens 111. In an embodiment, the scanning apparatus 110 may send a control signal in a wired or wireless manner to control at least one optical lens 111, the transfer apparatus 120, and the light source apparatus 130. The optical lens 111 may employ an area scan camera and/or a line scan camera. The line scan camera is relatively often used in dynamic scanning inspection to shoot while an object 101 is moving, thereby ensuring continuity of an inspection process. The transfer apparatus 120 is used to implement fully automated inspection. For example, the transfer apparatus 120 may transfer the object 101 to an inspection region and scan through the optical lens 111 disposed on a side of the inspection region to obtain information of the object 101 and perform subsequent analysis.

In different embodiments, the wafer scanning system 100 may employ various wafer scanning systems, such as an optical microscope system, a scanning electron microscope (SEM) system, a focused ion beam (FIB) microscope system, a laser microscope system, a transmission electron microscope (TEM) system, a scanning probe microscope (SPM) system, or other suitable optical image systems. Accordingly, when a different wafer scanning system is employed, the scanning information that the wafer scanning system 100 may obtain by scanning the surface of an object includes, for example, a haze value, surface roughness (Ra), an image parameter, and the like. For example, the image parameter includes a grayscale value, a luminance value, a contrast value, an RGB value, a saturation value, a color temperature value, and a Gamma value, but the disclosure is not limited thereto.

The light source apparatus 130 is used to provide a light source to support illumination for the object 101. The type of the light source apparatus 130 is, for example but not limited to, a parallel light lamp, a diffused light lamp, a dome-shaped lamp, or the like. The light source apparatus 130 may emit various types of light such as white light, red light, green light, blue light, ultraviolet light, and infrared light. In addition, the type of the light source apparatus 130 may be changed in correspondence with different types of the object 101. It should be noted that the disclosure does not limit the number of the scanning apparatus 110, the transfer apparatus 120, and the light source apparatus 130.

Figure 2:
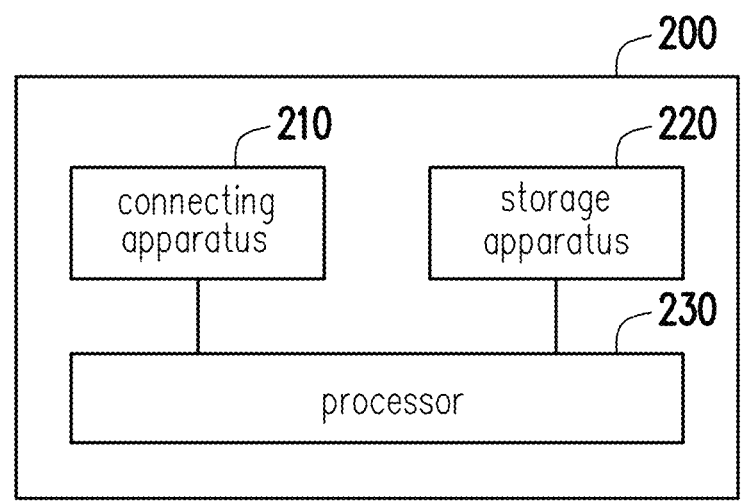
FIG. 2 is a schematic diagram of a wafer surface defect inspection apparatus according to an embodiment of the disclosure.

FIG. 2 is a schematic diagram of a wafer surface defect inspection apparatus according to an embodiment of the disclosure. With reference to FIG. 2, a wafer surface defect inspection apparatus 200 includes, but is not limited to, a connecting apparatus 210, a storage apparatus 220, and a processor 230. The wafer surface defect inspection apparatus 200 may be any electronic apparatus with computing capabilities such as a personal computer, a notebook computer, a server, or the like, but the disclosure is not limited thereto. The connecting apparatus 210 is used to connect the scanning apparatus 110 in a wired or wireless manner for receiving scanning information generated by the scanning apparatus 110 scanning a wafer.

The storage apparatus 220 may include a volatile storage medium and/or a non-volatile storage medium and may be used to store data. For example, the volatile storage medium may be random access memory (RAM), and the non-volatile storage medium may be read-only memory (ROM), solid state drive (SSD), traditional hard disk drive (HDD), other similar apparatuses, or a combination of these apparatuses for storing one or more instructions executed by the processor 230.

The processor 230 is coupled to the connecting apparatus 210 and the storage apparatus 220 and may access and execute the instruction recorded in the storage apparatus 220 to implement the wafer surface defect inspection method in the embodiments of the disclosure. In different embodiments, the processor 230 is, for example but not limited to, a central processing unit (CPU) or other programmable general-purpose or special-purpose microprocessor, a digital signal processor (DSP), a programmable controller, an application specific integrated circuit (ASIC), a programmable logic device (PLD), other similar apparatuses, or a combination of these apparatuses.

In a wafer processing process, after silicon carbide becomes silicon carbide ingots, some processing procedures are still required in the following. The processing procedures include slicing, rounding, grinding, etching, heat treatment, defect removal, and other processes. During slicing, grinding, and other different processing procedures, defects such as sawing patterns or grinding patterns may be left on the surface of a wafer, causing the surface to be uneven. After these procedures, a wafer is prone to generate a zebra-like pattern, a sun-like pattern, a wave-like pattern, or the like. Therefore, a sliced wafer needs to be ground to different extents to form a flat surface.

Figure 3:
FIG. 3 to FIG. 4 are schematic diagrams of a texture of a wafer according to an embodiment of the disclosure.
Figure 4:
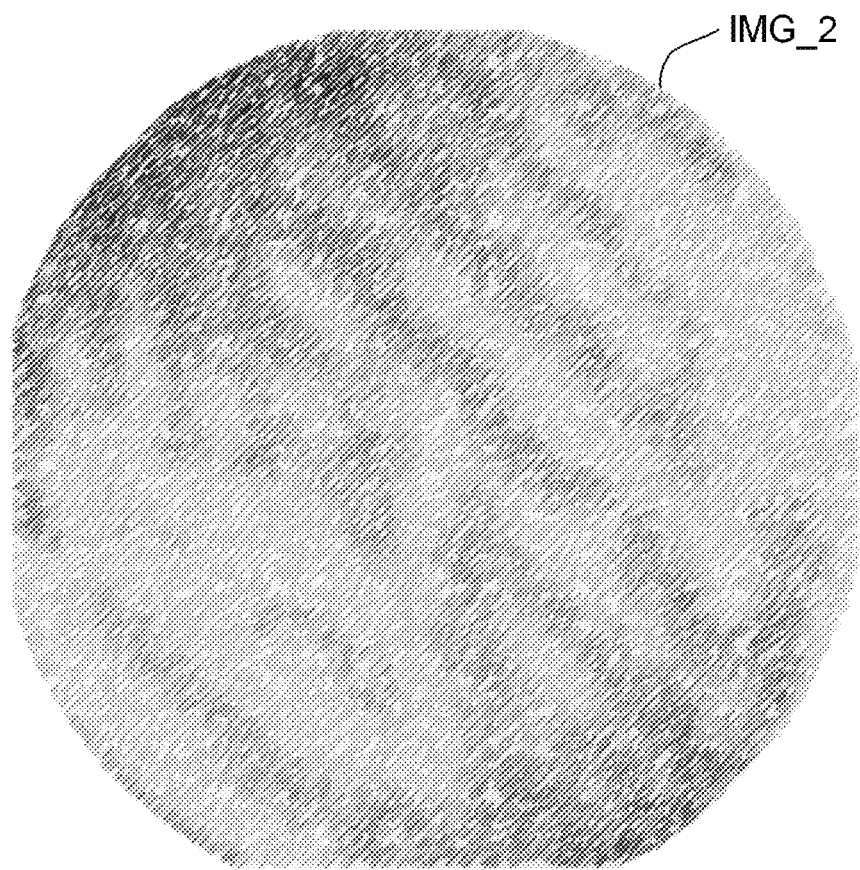

FIG. 3 to FIG. 4 are schematic diagrams of a texture of a wafer according to an embodiment of the disclosure. In wafer inspection, if a wafer image has a zebra-like pattern, a sun-like pattern, a wave-like pattern, or the like, it may be determined that the surface of the wafer corresponding to the wafer image is not flat. For example, an image IMG_1 in FIG. 3 shows that the corresponding wafer has a sun-like pattern, while an image IMG_2 in FIG. 4 shows that the corresponding wafer has a zebra-like pattern. However, erroneous determination may be caused due to varying interpretation by inspectors based on their own subjective standards for flatness. Hence, the wafer surface defect inspection method provided in the embodiment of the disclosure may solve this problem.

Figure 5:
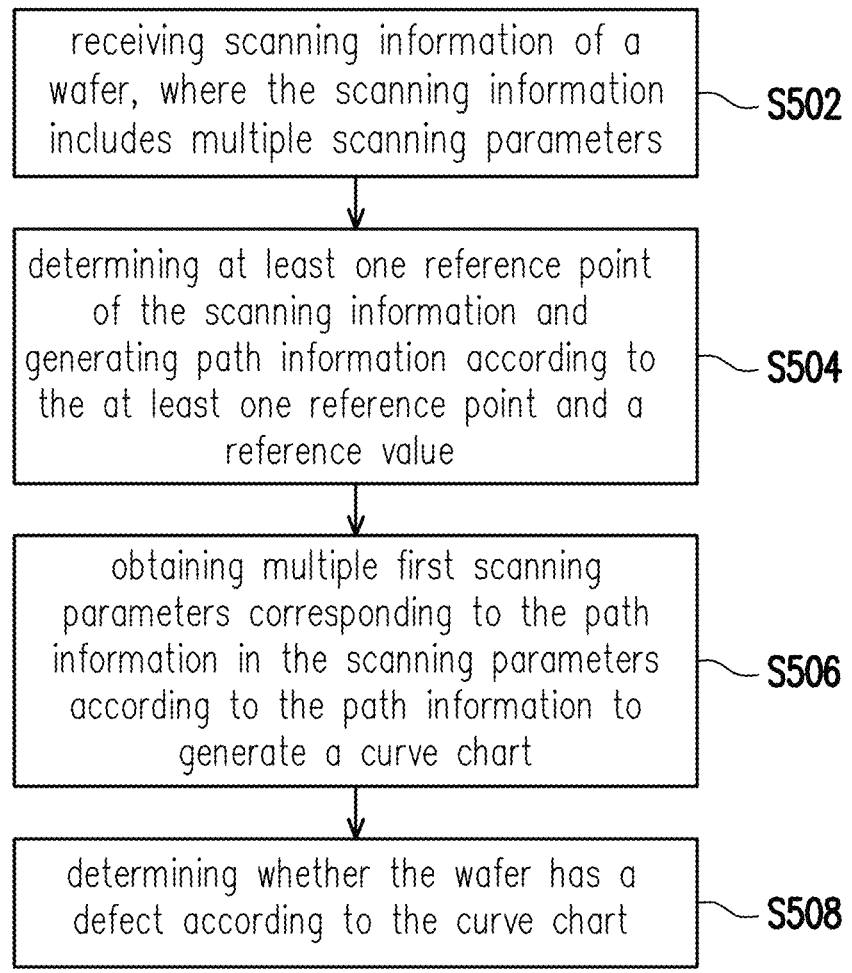
FIG. 5 is a flow chart of a wafer surface defect inspection method according to an embodiment of the disclosure.

FIG. 5 is a flow chart of a wafer surface defect inspection method according to an embodiment of the disclosure. With reference to FIG. 2 and FIG. 5 together, the method in this embodiment is adapted for the wafer surface defect inspection apparatus 200. Detailed steps of the method in this embodiment are described as follows with reference to elements of the wafer surface defect inspection apparatus 200 in FIG. 2 and FIG. 5.

It should be noted that each step in FIG. 5 may be implemented by multiple program codes or circuits, and the disclosure is not limited thereto. Furthermore, the method in FIG. 5 may be used with the following exemplary embodiments or may be used alone, and the disclosure is not limited thereto.

In step S502, the processor 230 receives scanning information of a wafer, where the scanning information includes multiple scanning parameters. Specifically, the scanning information may be formatted as a pixel array, with each pixel in the pixel array representing a specific position of the corresponding wafer and including a scanning parameter. The number of pixels in the array may be changed according to resolution capabilities of the scanning apparatus.

In step S504, the processor 230 determines at least one reference point of the scanning information and generates path information according to the at least one reference point and a reference value. In this embodiment, the reference point corresponds to a specific coordinate of the wafer. For example, the reference point may include the center of the wafer or other coordinate points. In addition, the reference value may be any reference information such as a wafer size parameter or a wafer processing parameter. For example, the wafer size parameter may include the size and radius of a wafer, and the wafer processing parameter may include a slice angle or the like, but the disclosure is not limited thereto. The slice angle refers to, with a dovetail groove fixing a wafer during slicing as the benchmark, an included angle between a flat position of the wafer and the dovetail groove. It should be noted that the reference value may be a value entered by an operator. For example, the slice angle is an angle entered by the operator slicing a wafer after confirming the flat position of the wafer.

Implementation details of generating path information are further described as follows.

Figure 6:
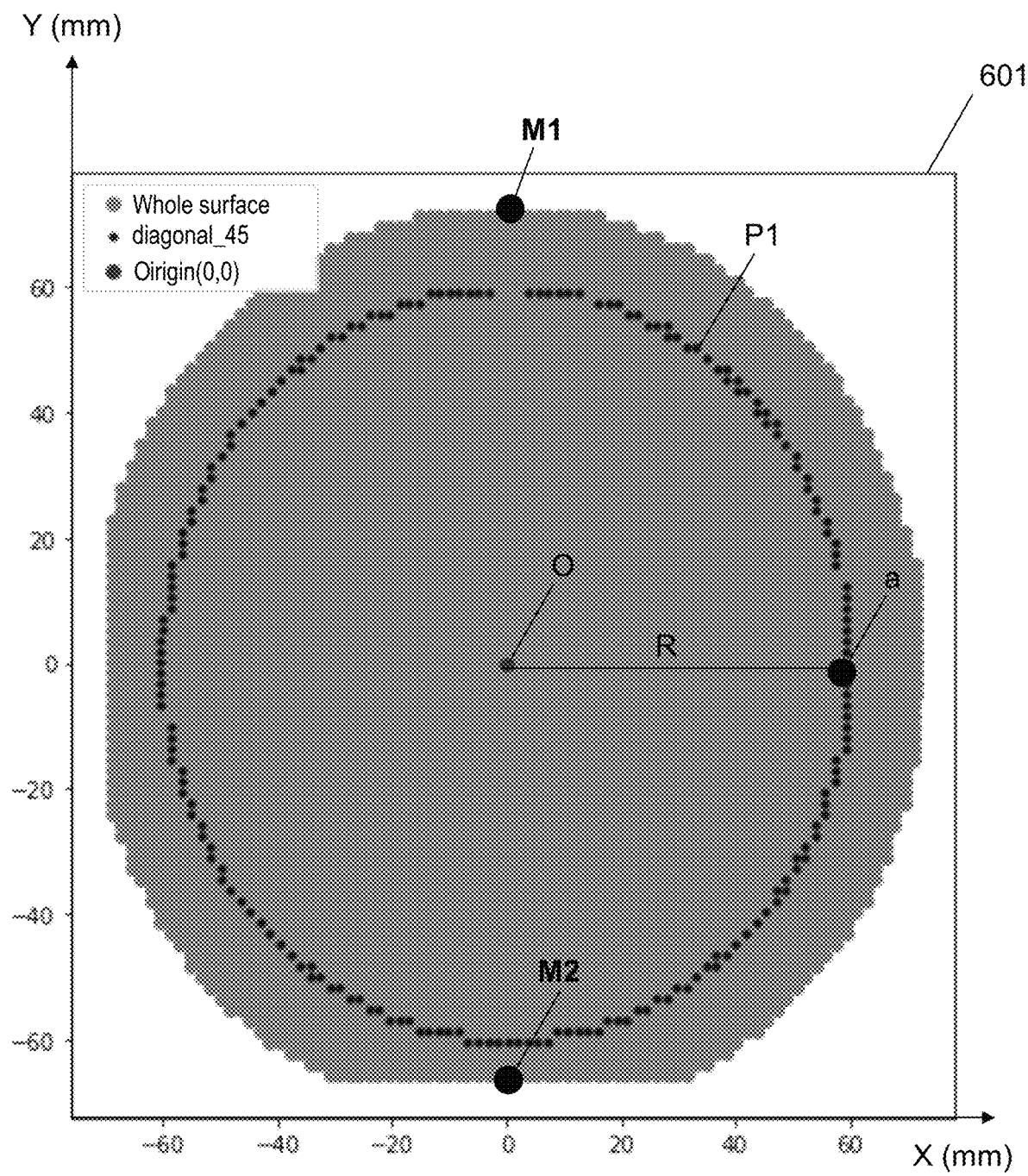
FIG. 6 is a schematic diagram of path information according to an embodiment of the disclosure.

FIG. 6 is a schematic diagram of path information according to an embodiment of the disclosure. Description in this embodiment is exemplified by generating a circular path. In this embodiment, the reference value includes a radius of a wafer. In this embodiment, the processor 230 calculates the center of the wafer corresponding to scanning information as a reference point. Next, the processor 230 determines a circular path according to the radius based on the reference point.

With reference to FIG. 6, which includes an image 601, the image 601 is a graphic schematic diagram of scanning information corresponding to a wafer. To facilitate description, it is assumed that the reference value includes a radius R of the wafer. Specifically, the processor 230 may, for example, calculate a median point of a pixel corresponding to a coordinate point M1 and a pixel corresponding to a coordinate point M2 in the pixel array of the scanning information (i.e., a center O in FIG. 6) as the reference point. The coordinate point M1 corresponds to a pixel having the maximum Y-coordinate Ymax among pixels corresponding to the wafer (with reference to the gray part of the image 601) in the pixel array of the scanning information. The coordinate point M2 corresponds to a pixel having the minimum Y-coordinate Ymin among pixels corresponding to the wafer in the pixel array of the scanning information. In following, with the center O as the center, the processor 230 generates a circular path P1 having the radius R. It should be noted that the disclosure does not limit how the center is calculated, and those skilled in the art may design their own methods for calculating the center based on the enlightenment of the above exemplary embodiment. In other embodiments, the processor 230 may further generate multiple circular paths according to different radii. For example, the processor 230 may generate multiple circular paths by scaling the radius R or scaling the circular path P1 according to a preset scaling ratio (such as 2/5, 3/5, or 4/5).

Figure 7:
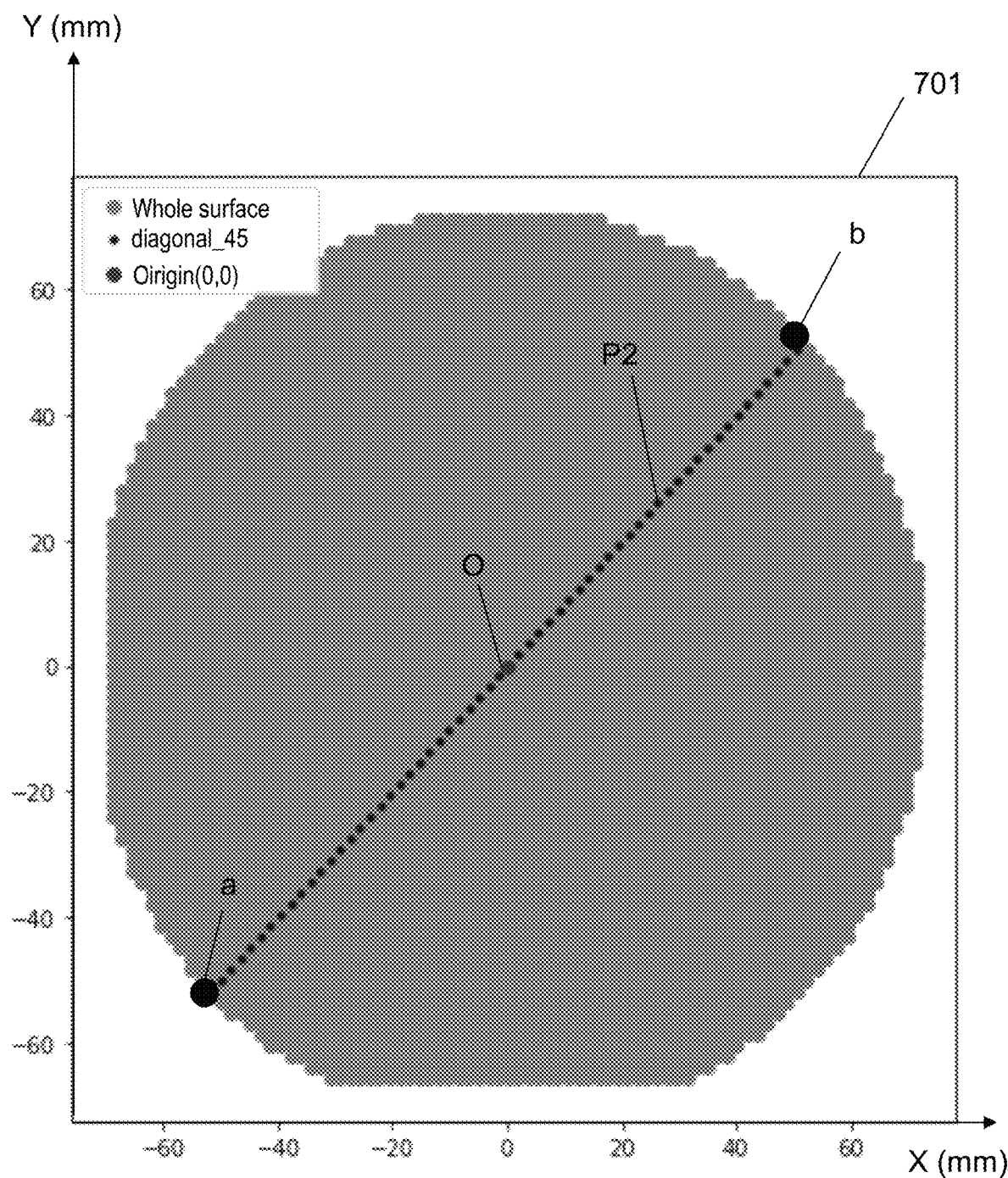
FIG. 7 is a schematic diagram of path information according to an embodiment of the disclosure.

FIG. 7 is a schematic diagram of path information according to an embodiment of the disclosure. Description in this embodiment is exemplified by generating a penetrating path. In this embodiment, the reference value includes a slice angle of a wafer. First, the processor 230 calculates a flat position of the scanning information and the center of the wafer corresponding to the scanning information. Next, the processor 230 calculates a median point of the flat position as a reference point (also referred to as a first reference point) and uses the center as another reference point (also referred to as a second reference point). In following, the processor 230 determines a reference path according to the first reference point and the second reference point.

After determining the reference path, the processor 230 determines a penetrating path according to the reference path and the slice angle. For example, the processor 230 may calculate a rotation angle according to the slice angle. Next, the processor 230 rotates the reference path according to the rotation angle to generate the penetrating path.

With reference to FIG. 7, which includes an image 701, the image 701 is a graphic schematic diagram of scanning information corresponding to a wafer. To facilitate description, it is assumed that the reference value includes a slice angle α of the wafer. FIG. 7 illustrates a penetrating path P2 that has a coordinate point a and a coordinate point b as two endpoints and passes through the center O. Regarding how the penetrating path is generated, reference may be made to the following paragraphs for specific details.

Figure 8A:
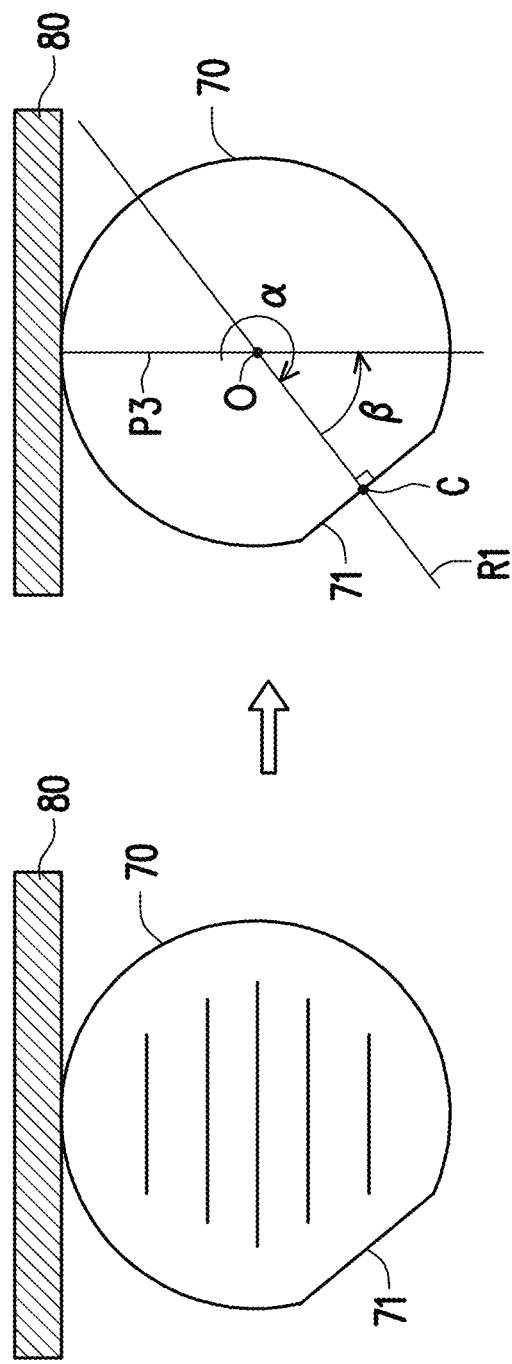
FIG. 8A is a schematic diagram of a process of generating a penetrating path according to an embodiment of the disclosure.
Figure 8B:
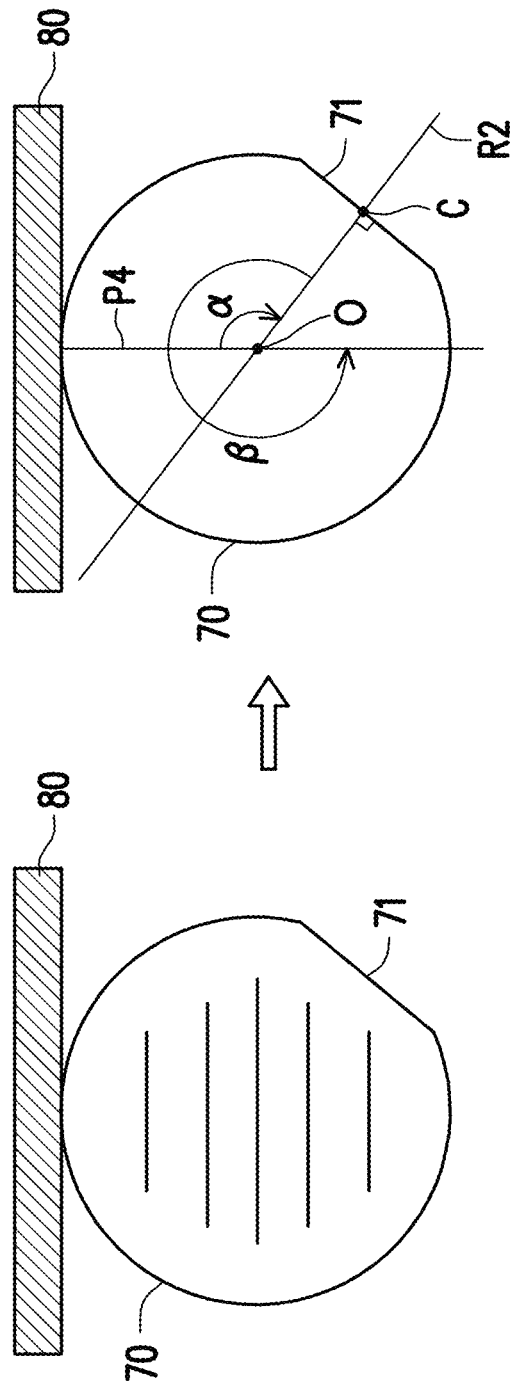
FIG. 8B is a schematic diagram of a process of generating a penetrating path according to another embodiment of the disclosure.

FIG. 8A is a schematic diagram of a process of generating a penetrating path according to an embodiment of the disclosure. FIG. 8B is a schematic diagram of a process of generating a penetrating path according to another embodiment of the disclosure. A dovetail groove 80 in FIG. 8A and FIG. 8B is illustrated for showing the relationship between the position of the dovetail groove 80 fixing the wafer and the slice angle during slicing the wafer. With reference to FIG. 8A and FIG. 8B, with the dovetail groove 80 as the benchmark, an included angle between a vertical line of a flat position 71 of a wafer 70 and a vertical line of the dovetail groove 80 in the clockwise direction is the slice angle α. In the embodiment of FIG. 8A, the processor 230 calculates the flat position 71 of the wafer 70 in the scanning information and the center O of the wafer corresponding to the scanning information. Next, the processor 230 calculates a median point c of the flat position 71 as the first reference point and uses the center O as the second reference point. In following, the processor 230 determines a reference path R1 according to the median point c and the center O. After determining the reference path R1, the processor 230 calculates a rotation angle β according to the slice angle α. Next, the processor 230 rotates the reference path R1 counterclockwise according to the rotation angle β and generates a penetrating path P3.

The calculation method of the rotation angle β varies according to the slice angle α. Taking FIG. 8A as an example, since the slice angle α is greater than 180°, the rotation angle β is equal to the slice angle α minus 180°. In addition, taking FIG. 8B as an example, since the slice angle α is less than 180°, the rotation angle β is equal to the slice angle α plus 180°. In the embodiment of FIG. 8B, the processor 230 rotates the reference path R2 counterclockwise according to the rotation angle β and generates a penetrating path P4. It should be noted that although the previous embodiment uses the vertical line of the dovetail groove as the benchmark, the included angle between the vertical line of the flat position of the wafer and the vertical line of the dovetail groove in the clockwise direction is the slice angle. However, those skilled in the art should understand that the included angle in the counterclockwise direction may also be the slice angle, and the rotation direction of rotating the reference path may be designed according to different included angle directions to generate the penetrating path. The disclosure is not limited the above.

With reference to FIG. 5 again, in step S506, the processor 230 obtains multiple first scanning parameters corresponding to the path information in the scanning parameters according to the path information to generate a curve chart.

Specifically, after generating the path information, the processor 230 obtains the scanning parameters (also referred to as the first scanning parameters) from the pixels corresponding to the path information in the scanning information along a direction of the path information. Next, the processor 230 generates the curve chart according to the first scanning parameters and a sequence of obtaining the first scanning parameters.

In following the embodiment of FIG. 6, the processor 230 may, starting from any point of the circular path P1 (such as the coordinate point a), obtain the first scanning parameters from the pixels corresponding to the circular path P1 in the scanning information along the clockwise or counterclockwise direction. In following the embodiment of FIG. 7, the processor 230 may, along the direction from the coordinate point a to the coordinate point b or the direction from the coordinate point b to the coordinate point a in the penetrating path P2, obtain the first scanning parameters from the pixels corresponding to the penetrating path P2 in the scanning information. As for obtaining the scanning parameters from the pixels corresponding to the path information in the scanning information according to the path information, it is a technical means well known to those in the art, and details are not described herein.

Figure 9:
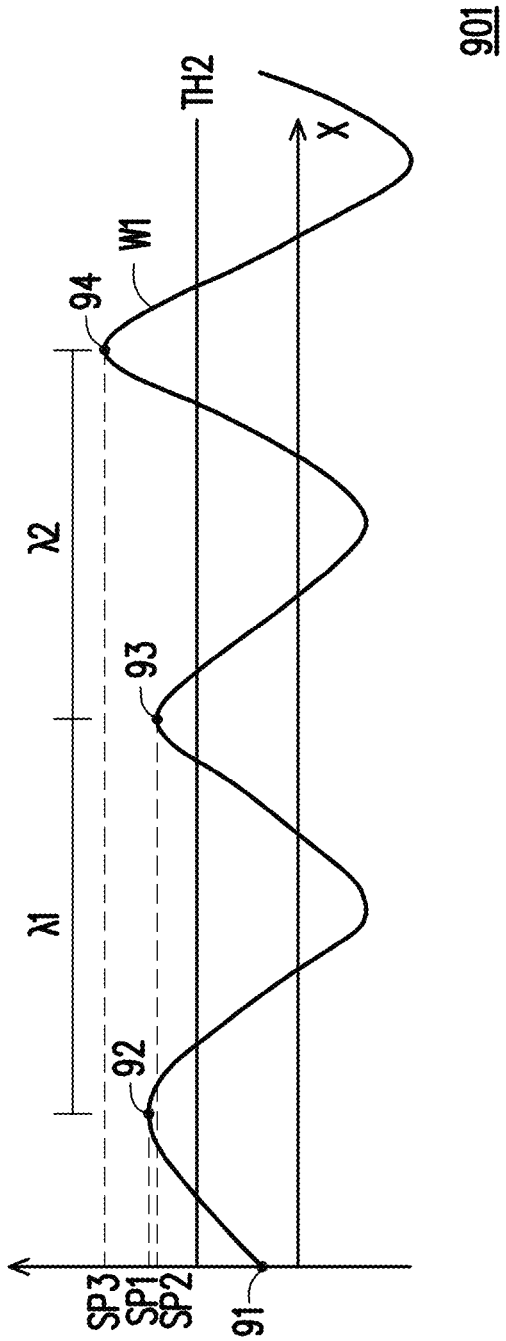
FIG. 9 is a schematic diagram of a curve chart according to an embodiment of the disclosure.

FIG. 9 is a schematic diagram of a curve chart according to an embodiment of the disclosure. FIG. 9 shows the relationship between the first scanning parameters and the sequence of obtaining the first scanning parameters. A curve chart 901 includes a curve W1. In the curve chart 901, the vertical axis represents the first scanning parameters, and the horizontal axis represents the sequence of obtaining the first scanning parameters. The processor 230 may generate the curve W1 according to the first scanning parameters and the sequence of obtaining the first scanning parameters. A starting point 91 of the curve W1 may correspond to the coordinate point a in FIG. 6 or the coordinate points a and b in FIG. 7. In this embodiment, the curve W1 presents a waveform, but the curve W1 may present different shapes according to different wafer conditions.

In step S508, the processor 230 determines whether the wafer has a defect according to the curve chart. When the wafer is not flat, the curve included in the curve chart generated by the previous step shows specific regularity. Therefore, the processor 230 may analyze the curve chart to determine whether the wafer has a defect (being not flat). In addition, the processor 230 may further determine a defect type of the wafer defect according to the curve chart. For example, the curve chart generated according to the circular path may be used to determine patterns such as sun-like patterns and cloud-like patterns, and the curve chart generated according to the penetrating path may be used to determine patterns such as zebra-like patterns and cloud-like patterns.

Specifically, the processor 230 may determine whether the wafer corresponding to the curve chart has a defect and also determine the defect type of the defect according to conditions such as whether the curve in the curve chart includes a regular sine wave and/or whether the value included in the curve exceeds a threshold. For example, the processor 230 may calculate distances between each pair of adjacent wave peaks or each pair of adjacent wave troughs in the curve chart and determine whether the curve includes a regular sine wave according to difference values between the distances. For example, when the difference values between the distances between each pair of adjacent wave peaks or each pair of adjacent wave troughs are all less than a threshold, the processor 230 determines that the curve includes a regular sine wave. When at least one of the difference values between the distances between each pair of adjacent wave peaks or each pair of adjacent wave troughs is not all less than the threshold, the processor 230 determines that the curve does not include a regular sine wave. It should be noted that the disclosure is not limited to the above method of determining a regular sine wave. Those skilled in the art should understand that there may be other implementation methods for determining whether the curve chart includes a regular sine wave, and details are not described herein.

In this embodiment, if the curve includes a regular sine wave (for example, the difference values between the distances between each pair of adjacent wave peaks or each pair of adjacent wave troughs are all less than a threshold, which is also referred to as a first threshold), and at least one of the first scanning parameters corresponding to the curve chart is greater than a threshold, which is also referred to as a second threshold, the processor 230 may determine that the wafer corresponding to the curve chart has a defect. Furthermore, if the curve chart for determining a defect is generated according to the circular path, it may be thereby determined that the wafer has a sun-like pattern, and then the processor 230 may give an instruction to a grinding machine for fine grinding on the chip. On the other hand, if the curve chart for determining a defect is generated according to the penetrating path, it may be thereby determined that the wafer has a zebra-like pattern, and then the processor 230 may give an instruction to the grinding machine for rough grinding on the chip.

In addition, if the curve does not include a regular sine wave (for example, at least one of the difference values between the distances is not less than the first threshold), and at least one of the first scanning parameters is greater than the second threshold, the processor 230 may also determine that the wafer has a defect. In this embodiment, if the curve chart for determining a defect is generated according to the circular path or the penetrating path, it may be thereby determined that the wafer has a cloud-like pattern, and then the processor 230 may give an instruction to the grinding machine for fine grinding on the chip. Finally, regardless of whether the curve includes a regular sine wave, when the first scanning parameters are all not greater than the second threshold, the processor 230 may determine that the wafer does not have a defect. The chip may be determined to be qualified and require no grinding.

In following the embodiment of FIG. 9, the curve W1 in the curve chart 901 includes wave peaks 92, 93, and 94. A distance $\lambda 1$ represents the difference value between the wave peak 92 and the wave peak 93, while a distance $\lambda 2$ represents the difference value between the wave peak 93 and the wave peak 94. In this embodiment, the difference value between the distance $\lambda 1$ and the distance $\lambda 2$ is less than the first threshold, and at least first scanning parameters SP1, SP2, and SP3 corresponding to the wave peaks 92, 93, and 94 are greater than a second threshold TH2, so the processor 230 determines that the wafer corresponding to the curve chart 901 has a defect.

Table 1 lists defect types and the determination conditions thereof in this embodiment. With reference to Table 1 below, if the curve includes a regular sine wave and at least one of the first scanning parameters is greater than the second threshold, the processor 230 may determine that the defect type is a sun-like pattern or a zebra-like pattern according to whether the curve chart is generated based on the circular path or the penetrating path. If the curve does not include a regular sine wave and at least one of the first scanning parameters is greater than the second threshold, the processor 230 may determine that the defect type is a cloud-like pattern. If the first scanning parameters are all not greater than the second threshold, regardless of whether the curve includes a regular sine wave, the processor 230 may determine that the wafer does not have a defect. It should be noted that the disclosure does not limit how the defect type is determined, and those skilled in the art may design their own conditions for determining different defect types based on the enlightenment of the above exemplary embodiment.

TABLE 1

| Path information | Curve including a regular sine wave | At least one of the first scanning parameters greater than the second threshold | Defect type |
|---|---|---|---|
| circular path | yes | yes | sun-like pattern |
| circular path | no | yes | cloud-like pattern |
| penetrating path | yes | yes | zebra-like pattern |
| penetrating path | no | yes | cloud-like pattern |
| circular/penetrating path | yes/no | no | none |

To sum up, the embodiments of the disclosure provide a wafer surface defect inspection method and a wafer surface defect inspection apparatus, which may extract parameters included in scanning information of a wafer according to path information to analyze whether the wafer has a defect, improving completeness of defect inspection. In addition, the inspection method provided in an embodiment of the disclosure further takes different characteristics of different wafer patterns into account during generation of path information, and generates the path information of different patterns to extract the parameters included in the scanning information for improving accuracy of defect inspection. Based on this, in the embodiments of the disclosure, the parameters for defect analysis in the scanning information may be effectively extracted through path analysis to facilitate rapid determination of defect types. Accordingly, a unified defect determination standard may be established, and probability of erroneous determination of defects may be reduced.

Although the disclosure has been described with reference to the above embodiments, they are not intended to limit the disclosure. It will be apparent to one of ordinary skill in the art that modifications to the described embodiments may be made without departing from the spirit and the scope of the disclosure. Accordingly, the scope of the disclosure will be defined by the attached claims and their equivalents and not by the above detailed descriptions.

What is claimed is:

1. A wafer surface defect inspection method, adapted for execution by a processor included in an electronic apparatus, the wafer surface defect inspection method comprising:
   receiving an image, including scanning information, of a wafer, wherein the scanning information is formatted as a pixel array, the pixel array comprises a plurality of pixels and a plurality of scanning parameters;
   determining at least one reference point from the plurality of pixels of the scanning information and generating path information according to the at least one reference point and a reference value, wherein the path information is a path with a specified shape, and the path with the specified shape is formed by extracting a plurality of first pixels from all of the pixels of the scanning information;
   obtaining a plurality of first scanning parameters corresponding to the plurality of first pixels that form the path information from the plurality of scanning parameters to generate a curve chart according to the first scanning parameters and a sequence of obtaining the first scanning parameters;
   in response to none of the first scan parameters exceeding a threshold for determining flatness, determining that the wafer does not have a defect;
   in response to at least one of the first scan parameters exceeding the threshold for determining flatness, determining that the wafer has the defect, and determining whether a curve in the curve chart includes a regular sine wave;
   in a case of determining that the wafer has the defect, determining a defect type of the defect based on the specified shape of the path and whether the curve includes the regular sine wave; and
   sending, through a connector assembly, an instruction corresponding to the defect type to a grinding machine having a grinding wheel to enable the grinding machine fine grinding or rough grinding on the wafer that has the defect through the grinding wheel.

2. The wafer surface defect inspection method according to claim 1, wherein the reference value comprises at least one radius and determines the at least one reference point of the scanning information, and forming the path with the specified shape comprises:
   calculating a center of the wafer corresponding to the scanning information as the at least one reference point; and
   determining, based on the at least one reference point, at least one circular path according to the at least one radius.

3. The wafer surface defect inspection method according to claim 2, wherein generating the curve chart comprises:
   obtaining the plurality of first scanning parameters from pixels corresponding to the at least one circular path in the scanning information along a direction of the at least one circular path; and
   generating the curve chart according to the plurality of first scanning parameters and a sequence of obtaining the plurality of first scanning parameters.

4. The wafer surface defect inspection method according to claim 1, wherein the reference value comprises a slice angle and determines the at least one reference point of the scanning information, and forming the path with the specified shape comprises:
   calculating a flat position of the scanning information and a center of the wafer corresponding to the scanning information;
   calculating a median point of the flat position as a first reference point and using the center as a second reference point;
   determining a reference path according to the first reference point and the second reference point; and
   determining a penetrating path according to the reference path and the slice angle.

5. The wafer surface defect inspection method according to claim 4, wherein the step of determining the penetrating path according to the reference path and the slice angle comprises:
calculating a rotation angle according to the slice angle; and
rotating the reference path according to the rotation angle to generate the penetrating path.

6. The wafer surface defect inspection method according to claim 4, wherein the step of obtaining the plurality of first scanning parameters corresponding to the plurality of first pixels that form the path information from the plurality of scanning parameters to generate the curve chart according to the first scanning parameters and the sequence of obtaining the first scanning parameters comprises:
obtaining the plurality of first scanning parameters from pixels corresponding to the penetrating path in the scanning information along a direction of the penetrating path; and
generating the curve chart according to the plurality of first scanning parameters and the sequence of obtaining the plurality of first scanning parameters.

7. The wafer surface defect inspection method according to claim 1, wherein determining whether the curve in the curve chart includes the regular sine wave comprises:
calculating a distance between each pair of adjacent wave peaks or each pair of adjacent wave troughs in the curve chart;
in response to difference values between the distances are all less than a first threshold, determining that the curve includes the regular sine wave; and
in response to at least one of the difference values between the distances is not less than the first threshold, determining that the curve does not include the regular sine wave.

8. The wafer surface defect inspection method according to claim 1, wherein a number of the defect type is 3, comprising a first defect type, a second defect type and a third defect type,
the step of determining the defect type of the defect based on the specified shape of the path and whether the curve includes the regular sine wave comprises:
if the curve chart is generated based on a circular path, the curve includes the regular sine wave and at least one of the first scanning parameters is greater than a second threshold, determining that the defect type is the first defect type;
if the curve chart is generated based on a penetrating path, the curve includes the regular sine wave and at least one of the first scanning parameters is greater than the second threshold, determining that the defect type is the second defect type;
if the curve does includes the regular sine wave and at least one of the first scanning parameters is greater than the second threshold, determining that the defect type is the third defect type; and
if the first scanning parameters are all not greater than the second threshold, determining that the wafer does not have the defect.

9. The wafer surface defect inspection method according to claim 1, wherein the plurality of scanning parameters is generated by an optical lens of a scanning apparatus scanning the wafer, and the plurality of scanning parameters comprise at least one of a haze value, a surface roughness value, and an image parameter.

10. The wafer surface defect inspection method according to claim 9, wherein the image parameter comprises at least one of a grayscale value, a luminance value, a contrast value, an RGB value, a saturation value, a color temperature value, and a Gamma value.

11. A wafer surface defect inspection apparatus, comprising:
a connector assembly is configured to connect a scanning apparatus in a wired or wireless manner to receive an image, including scanning information, generated by an optical lens of the scanning apparatus scanning a wafer;
a storage apparatus, storing one or a plurality of instructions; and
a processor, coupled to the connector assembly and the storage apparatus and configured to execute the one or the plurality of instructions to perform operations comprising:
receiving the scanning information, wherein the scanning information is formatted as a pixel array, the pixel array comprises a plurality of pixels and a plurality of scanning parameters;
determining at least one reference point from the plurality of pixels of the scanning information and generating path information according to the at least one reference point and a reference value, wherein the path information is a path with a specified shape, and the path with the specified shape is formed by extracting a plurality of first pixels from all of the pixels of the scanning information;
obtaining a plurality of first scanning parameters corresponding to the plurality of first pixels that form the path information from the plurality of scanning parameters to generate a curve chart according to the first scanning parameters and a sequence of obtaining the first scanning parameters;
in response to none of the first scan parameters exceeding a threshold for determining flatness, determining that the wafer does not have a defect;
in response to at least one of the first scan parameters exceeding the threshold for determining flatness, determining that the wafer has the defect, and determining whether a curve in the curve chart includes a regular sine wave;
in a case of determining that the wafer has the defect, determining a defect type of the defect based on the specified shape of the path and whether the curve includes the regular sine wave; and
sending, through the connector assembly, an instruction corresponding to the defect type to a grinding machine having a grinding wheel to enable the grinding machine fine grinding or rough grinding on the wafer that has the defect through the grinding wheel.

12. The wafer surface defect inspection apparatus according to claim 11, wherein the reference value comprises at least one radius and determines the at least one reference point of the scanning information, and the processor is configured to execute the one or the plurality of instructions to:
calculate a center of the wafer corresponding to the scanning information as the at least one reference point; and
determine, based on the at least one reference point, at least one circular path according to the at least one radius.

13. The wafer surface defect inspection apparatus according to claim 12, wherein the processor is configured to execute the one or the plurality of instructions to:

obtain the plurality of first scanning parameters from pixels corresponding to the at least one circular path in the scanning information along a direction of the at least one circular path; and generate the curve chart according to the plurality of first scanning parameters and a sequence of obtaining the plurality of first scanning parameters.

14. The wafer surface defect inspection apparatus according to claim 11, wherein the reference value comprises a slice angle and determines the at least one reference point of the scanning information, and the processor is configured to execute the one or the plurality of instructions to:

calculate a flat position of the scanning information and a center of the wafer corresponding to the scanning information;

calculate a median point of the flat position as a first reference point and using the center as a second reference point;

determine a reference path according to the first reference point and the second reference point; and determine a penetrating path according to the reference path and the slice angle.

15. The wafer surface defect inspection apparatus according to claim 14, wherein the processor is configured to execute the one or the plurality of instructions to:

calculate a rotation angle according to the slice angle; and rotate the reference path according to the rotation angle to generate the penetrating path.

16. The wafer surface defect inspection apparatus according to claim 14, wherein the processor is configured to execute the one or the plurality of instructions to:

obtain the plurality of first scanning parameters from pixels corresponding to the penetrating path in the scanning information along a direction of the penetrating path; and generate the curve chart according to the plurality of first scanning parameters and a sequence of obtaining the plurality of first scanning parameters.

17. The wafer surface defect inspection apparatus according to claim 11, wherein the processor is configured to execute the one or the plurality of instructions to:

calculate a distance between each pair of adjacent wave peaks or each pair of adjacent wave troughs in the curve chart;

in response to difference values between the distances are all less than a first threshold, determine that the curve includes the regular sine wave; and in response to at least one of the difference values between the distances is not less than the first threshold, determine that the curve does not include the regular sine wave.

18. The wafer surface defect inspection apparatus according to claim 11, wherein a number of the defect type is 3, comprising a first defect type, a second defect type and a third defect type, the processor if configured to execute the one or the plurality of instructions to perform operations comprising:

if the curve chart is generated based on a circular path, the curve includes the regular sine wave and at least one of the first scanning parameters is greater than a second threshold, determining that the defect type is the first defect type;

if the curve chart is generated based on a penetrating path, the curve includes the regular sine wave and at least one of the first scanning parameters is greater than the second threshold, determining that the defect type is the second defect type;

if the curve does includes the regular sine wave and at least one of the first scanning parameters is greater than the second threshold, determining that the defect type is the third defect type; and if the first scanning parameters are all not greater than the second threshold, determining that the wafer does not have the defect.

19. The wafer surface defect inspection apparatus according to claim 11, wherein the plurality of scanning parameters are generated by the scanning apparatus scanning the wafer, and the plurality of scanning parameters comprise at least one of a haze value, a surface roughness value, and an image parameter.

20. The wafer surface defect inspection apparatus according to claim 19, wherein the image parameter comprises at least one of a grayscale value, a luminance value, a contrast value, an RGB value, a saturation value, a color temperature value, and a Gamma value.

* * * * *